(12) United States Patent
Lalli et al.

(10) Patent No.: US 10,687,699 B2
(45) Date of Patent: Jun. 23, 2020

(54) LIGHTING MODULE FOR A MEDICAL DEVICE AND METHODS FOR USING THE SAME

(71) Applicant: CEEK Enterprises, Portland, OR (US)

(72) Inventors: Maria Lalli, Portland, OR (US); Wesley Hare, Portland, OR (US); Katie Lee, Portland, OR (US); Christian Freissler, Portland, OR (US); Chase Thompson, Portland, OR (US); Jia Lu Ni, Portland, OR (US)

(73) Assignee: CEEK Enterprises, Portland, OR (US)

( * ) Notice: Subject to any disclaimer, the term of this patent is extended or adjusted under 35 U.S.C. 154(b) by 88 days.

(21) Appl. No.: 15/468,934

(22) Filed: Mar. 24, 2017

(65) Prior Publication Data
US 2018/0263480 A1  Sep. 20, 2018

Related U.S. Application Data

(60) Provisional application No. 62/473,169, filed on Mar. 17, 2017.

(51) Int. Cl.
*A61B 1/06* (2006.01)
*A61B 1/00* (2006.01)
*A61B 1/303* (2006.01)
*A61B 1/32* (2006.01)

(52) U.S. Cl.
CPC ........ *A61B 1/0684* (2013.01); *A61B 1/00105* (2013.01); *A61B 1/00131* (2013.01); *A61B 1/0676* (2013.01); *A61B 1/303* (2013.01); *A61B 1/32* (2013.01)

(58) Field of Classification Search
CPC ......... A61B 1/06; A61B 1/0684; A61B 1/303; A61B 1/32
See application file for complete search history.

(56) References Cited

U.S. PATENT DOCUMENTS

| | | |
|---|---|---|
| 2,524,881 A | 10/1950 | Chambers |
| 3,592,199 A | 7/1971 | Ostensen |
| 3,675,641 A | 7/1972 | Fiore |
| 3,716,047 A | 2/1973 | Moore et al. |
| 3,789,835 A | 2/1974 | Whitman |
| 3,851,642 A | 12/1974 | McDonald |

(Continued)

FOREIGN PATENT DOCUMENTS

| | | |
|---|---|---|
| CN | 1565664 A | 1/2005 |
| WO | WO-9825512 A1 | 6/1998 |

(Continued)

OTHER PUBLICATIONS

"EBBARED Battery-operated clamp spotlight," Ikea, https://web.archive.org/web/20161123013138/http://www.ikea.com/us/en/catalog/products/40251930/.

*Primary Examiner* — Christopher J Beccia
(74) *Attorney, Agent, or Firm* — Mintz Levin Cohn Ferris Glovsky and Popeo PC; Marc Morley; Melissa Brayman

(57) ABSTRACT

A lighting module includes a housing portion, a clip portion having a receiving space between configured to receive a speculum, an arm portion extending from the clip portion and including a lighting element, and a power source electrically connected to the lighting element. Also, a speculum assembly including a speculum and a lighting module is disclosed. Finally, a method of using a lighting module is disclosed.

21 Claims, 7 Drawing Sheets

(56) References Cited

U.S. PATENT DOCUMENTS

| | | |
|---|---|---|
| 4,006,738 A | 2/1977 | Moore et al. |
| 4,067,323 A | 1/1978 | Troutner et al. |
| 4,156,424 A | 5/1979 | Burgin |
| 4,300,541 A | 11/1981 | Burgin |
| 4,337,763 A | 7/1982 | Petrassevich |
| 4,344,419 A | 8/1982 | Burgin |
| 4,380,998 A | 4/1983 | Kieffer et al. |
| 4,502,468 A | 3/1985 | Burgin |
| 4,562,832 A | 1/1986 | Wilder et al. |
| 4,566,439 A | 1/1986 | Burgin |
| 4,597,383 A | 7/1986 | Vanderbel |
| 4,619,248 A | 10/1986 | Walsh |
| 4,638,792 A | 1/1987 | Burgin |
| 4,905,670 A | 3/1990 | Adair |
| 5,026,368 A | 6/1991 | Adair |
| 5,143,054 A | 9/1992 | Adair |
| 5,179,938 A | 1/1993 | Lonky |
| 5,329,938 A | 7/1994 | Lonky |
| 5,465,709 A | 11/1995 | Dickie et al. |
| 5,499,964 A | 3/1996 | Beck et al. |
| 5,716,329 A | 2/1998 | Dieter |
| 5,785,648 A | 7/1998 | Min |
| 5,846,249 A | 12/1998 | Thompson |
| 5,865,729 A | 2/1999 | Meehan et al. |
| 5,873,820 A | 2/1999 | Norell |
| 6,004,265 A | 12/1999 | Hsu et al. |
| 6,048,308 A | 4/2000 | Strong |
| 6,176,824 B1 | 1/2001 | Davis |
| 6,379,296 B1 | 4/2002 | Baggett |
| 6,394,950 B1 | 5/2002 | Weiss |
| 6,432,049 B1 | 8/2002 | Banta et al. |
| 6,450,952 B1 | 9/2002 | Rioux et al. |
| 6,589,168 B2 | 7/2003 | Thompson |
| 6,595,917 B2 | 7/2003 | Nieto |
| 6,830,547 B2 | 12/2004 | Weiss |
| 7,014,340 B2 | 3/2006 | Bettis |
| 7,311,663 B2 | 12/2007 | Marcotte |
| 7,553,020 B2 | 6/2009 | Goldfain et al. |
| 7,631,981 B2 | 12/2009 | Miller et al. |
| 7,749,162 B2 | 7/2010 | Balas |
| 7,758,203 B2 | 7/2010 | McMahon et al. |
| 7,758,206 B2 | 7/2010 | Kim |
| 8,083,673 B2 | 12/2011 | Rosen |
| 8,096,945 B2 | 1/2012 | Buchok et al. |
| 8,142,352 B2 | 3/2012 | Vivenzio et al. |
| 8,157,728 B2 | 4/2012 | Danna et al. |
| 8,267,855 B2 | 9/2012 | Barker |
| 8,376,942 B2 | 2/2013 | Krauter et al. |
| 8,388,523 B2 | 3/2013 | Vivenzio et al. |
| 8,435,175 B2 | 5/2013 | Mcmahon et al. |
| 8,808,175 B2 | 8/2014 | Deitch et al. |
| 8,821,395 B2 | 9/2014 | Mcmahon et al. |
| 8,876,711 B2 | 11/2014 | Lin et al. |
| 9,301,673 B2 | 4/2016 | Sun et al. |
| 9,314,149 B2 | 4/2016 | Vivenzio et al. |
| 9,332,898 B2 | 5/2016 | McMahon et al. |
| 9,532,706 B2 | 1/2017 | McMahon et al. |
| 2003/0176772 A1 | 9/2003 | Yang |
| 2005/0085699 A1* | 4/2005 | Weiss ............... A61B 1/303 600/221 |
| 2007/0156022 A1* | 7/2007 | Patel ............... A61B 1/267 600/199 |
| 2007/0255110 A1 | 11/2007 | Wax et al. |
| 2008/0228038 A1 | 9/2008 | McMahon et al. |
| 2008/0306345 A1 | 12/2008 | Balas |
| 2009/0076334 A1 | 3/2009 | Chen |
| 2009/0198108 A1 | 8/2009 | Chen et al. |
| 2010/0094092 A1 | 4/2010 | Barker |
| 2010/0191067 A1 | 7/2010 | Chen |
| 2010/0305406 A1 | 12/2010 | Braun et al. |
| 2011/0237902 A1 | 9/2011 | Rosen |
| 2012/0078060 A1 | 3/2012 | Swift |
| 2012/0108907 A1 | 5/2012 | Fitipaldi et al. |
| 2014/0039266 A1 | 2/2014 | Porat |
| 2014/0309499 A1 | 10/2014 | Swift |
| 2015/0238070 A1 | 8/2015 | Lia et al. |
| 2016/0038012 A1* | 2/2016 | McMahon ............... A61B 1/06 600/210 |

FOREIGN PATENT DOCUMENTS

| | | |
|---|---|---|
| WO | WO-2006/107877 A2 | 10/2006 |
| WO | WO-2006/107878 A2 | 10/2006 |
| WO | WO-2006/121530 A2 | 11/2006 |
| WO | WO-2008/080033 A2 | 7/2008 |
| WO | WO-2008/080040 A1 | 7/2008 |
| WO | WO-2009/149232 A2 | 12/2009 |

* cited by examiner

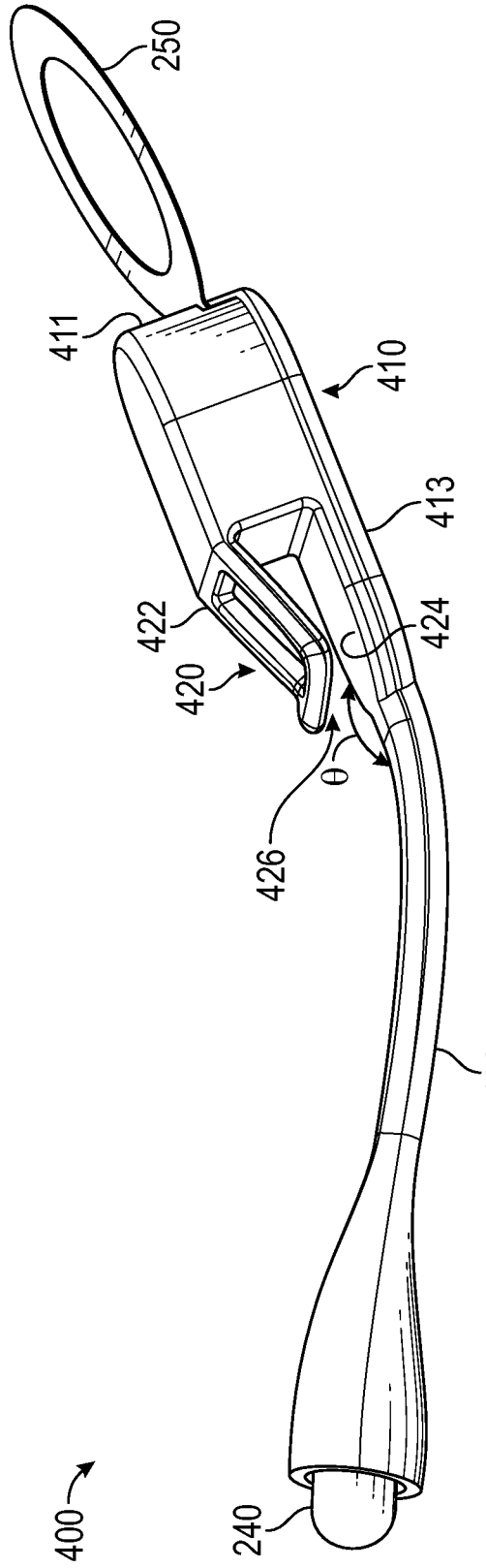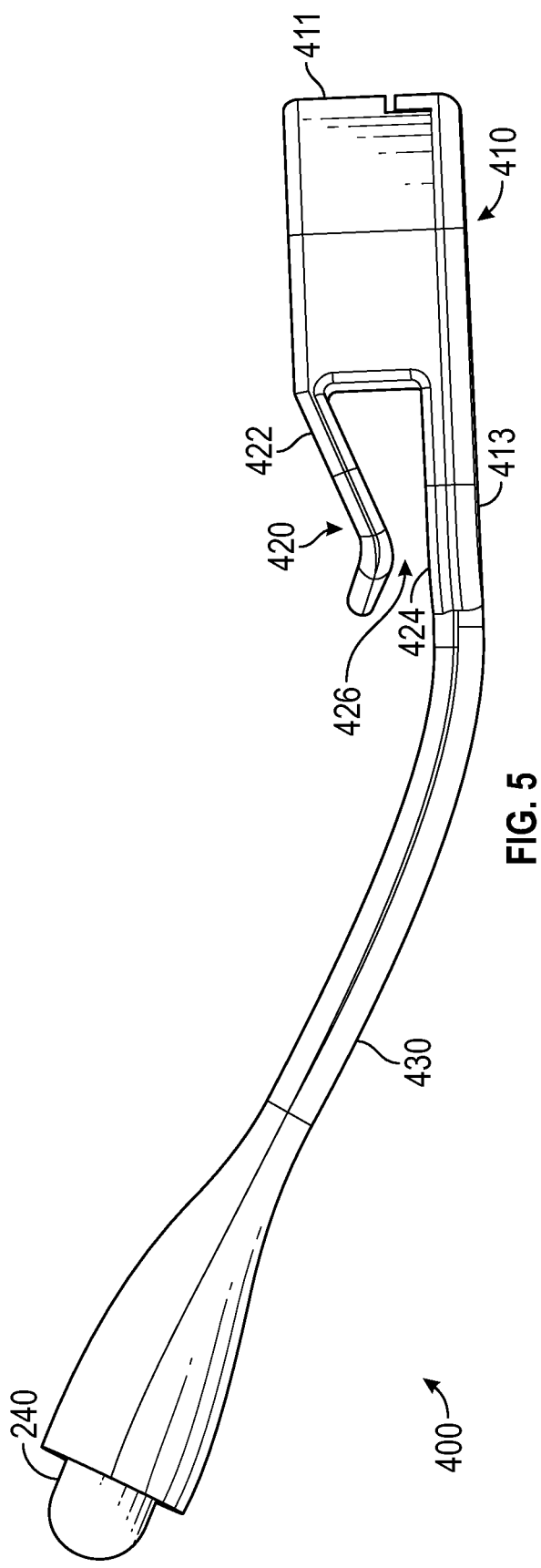

LIGHTING MODULE FOR A MEDICAL DEVICE AND METHODS FOR USING THE SAME

CROSS-REFERENCED TO RELATED APPLICATIONS

This application claims the benefit of U.S. Provisional Patent Application No. 62/473,169 entitled "Lighting Module for a Medical Device and Methods for Using the Same," which was filed on Mar. 17, 2017, the contents of which are all incorporated by reference herein.

BACKGROUND

The present disclosure relates generally to the field of illumination devices, and specifically to a universal lighting module for a medical device which facilitates medical examination of a patient.

A speculum is a medical tool used to provide visualization into a body cavity. Speculums or specula are traditionally used for viewing the vaginal cavity for gynecology patients. The traditional vaginal speculum consists of two bills with a hinge and a handle. The bills are inserted into the body cavity in a closed position and separated by squeezing two pieces of the handle together, or depressing a thumb lever, thereby dilating the vagina and providing visualization and accessibility of the vagina, the cervix, and surrounding areas.

Some specula include an integrated lightning module configured to provide illumination of the vaginal cavity of a patient when an operator is using a speculum for medical inspection of the vaginal cavity or for a medical procedure.

Embodiments herein generally relate to a universal lighting module which is easily attachable to and detachable from a speculum, and which is adjustable in position on a speculum such that an operator can adjust the direction of illumination provided by the lighting module. The lighting module may overcome many drawbacks of existing lighting systems. For example, described herein according to some embodiments is a lighting module that can be universally and removably attached to various types and sizes of speculum, and specula having different shapes and configurations.

SUMMARY OF THE INVENTION

One embodiment of the present disclosure relates to a lighting module including a housing portion, a clip portion which includes a receiving portion for receiving a portion of a medical device, an arm portion extending from the clip portion and including a lighting element at a distal end of the arm portion, and a power source electrically connected to the lighting element.

One embodiment of the present disclosure relates to a lighting module including a housing portion which includes a base plate and a front plate, a clip portion which includes a first flange and a second flange for receiving a portion of a medical device, an arm portion extending from one of the first flange and the second flange and including a lighting element at a distal end of the arm portion, and a power source electrically connected to the lighting element.

According to one aspect, the lighting module also includes an activation mechanism for providing power to the lighting element. According to one aspect, the activation mechanism is a pull tab between a first and a second battery and configured to prevent discharge of the batteries prior to operation of the lighting element such that when the pull tab is removed, the first battery and the second battery become electrically coupled to provide power to the lighting element.

According to one aspect, the medical device is a speculum. According to one aspect, the arm portion is configured to be disposed against a surface of a bill of the speculum. According to one aspect, the arm portion is adjustable. According to one aspect, the arm portion is flexible.

According to one aspect, at least one of the first flange and the second flange is deflectable such that the receiving space is adjustable. According to one aspect, at least one of the first flange and the second flange is deflectable to adapt to a variety of wall thicknesses such that the receiving space receives a different portion of the device. According to one aspect, a top surface of the top plate includes a soft portion. According to one aspect, the clip portion includes a grip on a surface facing the receiving space. According to one aspect, the grip is a texturized material. According to one aspect, the grip is an extended portion of the first flange or the second flange that extends into the receiving area.

According to one aspect, the lighting element is a LED. According to one aspect, the power source is at least one battery. According to one aspect, the power source is two batteries electrically connected together.

According to one aspect, the lighting module is disposable. According to one aspect, the lighting module is reusable.

According to a further embodiment of the present disclosure, a speculum assembly includes a speculum and the lighting module including a housing portion which includes a base plate and front plate, a clip portion which includes a first flange, a second flange, and a receiving space between the first flange and the second flange for receiving a portion of a speculum, an arm portion extending from one of the first flange and the second flange and including a lighting element at a distal end of the arm portion, and a power source electrically connected to the lighting element.

According to a still further embodiment of the present disclosure, a method for using the lighting module is disclosed. The method includes attaching a lighting module to a medical device. The lighting module includes a housing portion which includes a base plate and front plate, a clip portion which includes a first flange, a second flange, and a receiving space between the first flange and the second flange for receiving a portion of the medical device, an arm portion extending from one of the first flange and the second flange and including a lighting element at a distal end of the arm portion, and a power source electrically connected to the lighting element. The method also includes positioning the medical device for performing a procedure on a patient, providing power to the lighting element of the lighting module.

According to one aspect, the method further includes adjusting a position of the lighting element relative to the speculum to adjust a direction of the illumination from the lighting element. According to one aspect, the adjusting the position of the lighting element includes moving the lighting module such that the receiving space receives a different portion of the speculum. According to one aspect, the adjusting the position of the lighting element includes adjusting the arm portion of the lighting module.

According to one aspect, the lighting module further includes an activation mechanism for providing power to the lighting element and the step of providing power to the lighting element includes activating the activation mechanism.

BRIEF DESCRIPTION OF THE DRAWINGS

FIG. 4 is a perspective view of a lighting module according to another exemplary embodiment.

FIG. 5 is a side view of the lighting module of FIG. 4.

FIG. 9 is a front perspective view illustrating the speculum assembly shown in FIG. 2 in a state when the lighting element of the lighting module is turned on.

DETAILED DESCRIPTION

Figure 1:
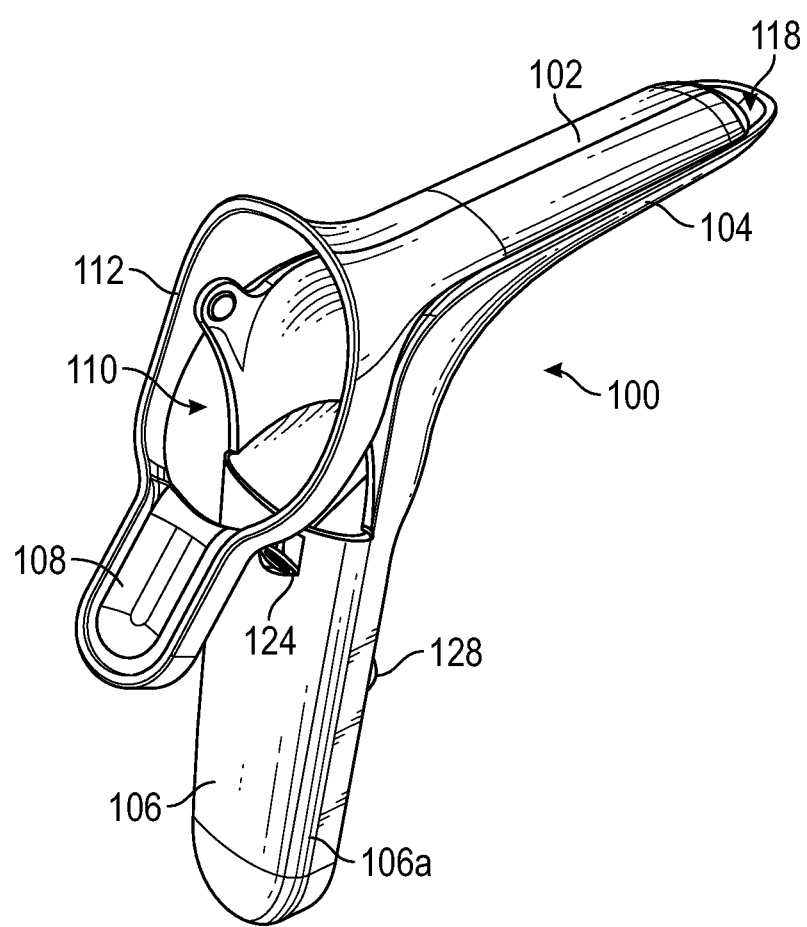
FIG. 1 is a rear perspective view of a medical device on which a lighting module according to one aspect may be used.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. The detailed description is intended as a description of exemplary embodiments and is not intended to represent the only embodiments which may be practiced. The term "exemplary," as used herein, means "serving as an example, instance, or illustration," and should not necessarily be construed as preferred or advantageous over other embodiments. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and form part of this disclosure.

Referring to the figures generally, a universal lighting module for a medical device is shown. The universal lighting module disclosed herein is configured to be attachable to and removable from a medical device such that the lighting module is usable by an operator (e.g., a physician, a nurse, a mid-wife, etc.) during a medical examination or procedure. Without being limited thereto, the universal lighting module disclosed herein is configured to be attachable to and removable from a medical speculum such that the lighting module is usable by an operator (e.g., a physician, a nurse, a mid-wife, etc.) during a medical examination or procedure (e.g., a pap smear, a vaginal inspection, etc.) on a female patient. Though the universal lighting module is shown for use on a vaginal speculum, its use is not limited thereto and the universal lighting module may be used on a variety of medical speculum and/or other medical devices which are used during a medical examination or procedure. Furthermore, the universal lighting module may be used on speculum having designs, shapes, configurations, and features other than those of the speculum shown in the figures, which is presented as an example only. The speculum may be made of metal or plastic, and may have a variety of other features that may not be shown or may be different than those shown in the figures.

The lighting module includes one or more illumination elements configured to allow better visualization of a body cavity in which a medical speculum is inserted. By providing the better visualization, the lighting module facilitates medical examination of a patient's vaginal body cavity and/or medical procedures operated on the vaginal body cavity.

Referring to FIG. 1, a speculum is shown as speculum 100 having an upper bill 102, a lower bill 104, a handle 106, a viewing window 110 formed by window frame 112, and an actuation mechanism 108. The lower bill 104 and the handle 106 are formed together as a unitary body portion. The upper bill 102 is rotatably coupled to a transition portion (not shown) between the lower bill 104 and the handle 106 such that the upper bill is movable between an open position and a closed position when the actuation mechanism, such as the actuation tab 108 is manipulated.

When the bills 102 and 104 are in the closed position, the speculum 100 can be inserted in a patient's vagina. An operator places the end 118 in line with an opening of the vagina and applies a force along a longitudinal axis of the bills 102 and 104 to push the bills 102 and 104 into the vagina. The operator may position the speculum 100 at a depth of the vagina to provide a clear view of the cervix when the bills 102 and 104 of the speculum are opened. The speculum 100 may be inserted so that the end 118 of the bills 102 and 104 are located below the cervix. Once the bills 102 and 104 are separated, the cervix may then fall into the viewing window created by the separation of the bills 102 and 104. Alternatively, the speculum may need to be shifted in different directions in order to view the cervix properly.

A universal lighting module is configured to provide visualization of the cervix and vaginal canal by illumination from a lighting element. The universal lighting module is configured to provide freedom of placement and easy adjustability during use. Finally, the embodiments of the universal lighting module herein disclosed have a simple and minimal design to achieve lower production costs.

Figure 2:
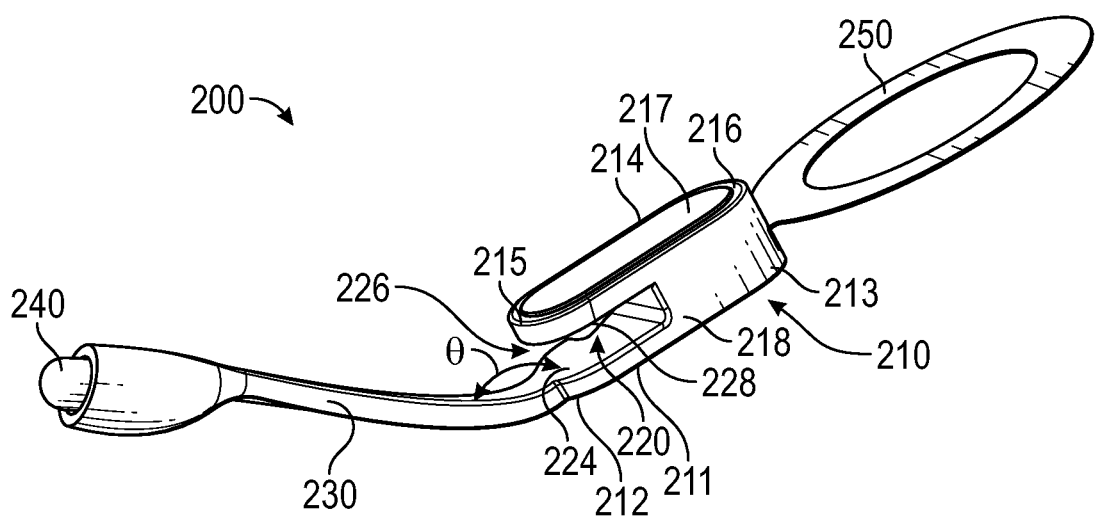
FIG. 2 is a perspective view of a lighting module according to an exemplary embodiment.
Figure 3:
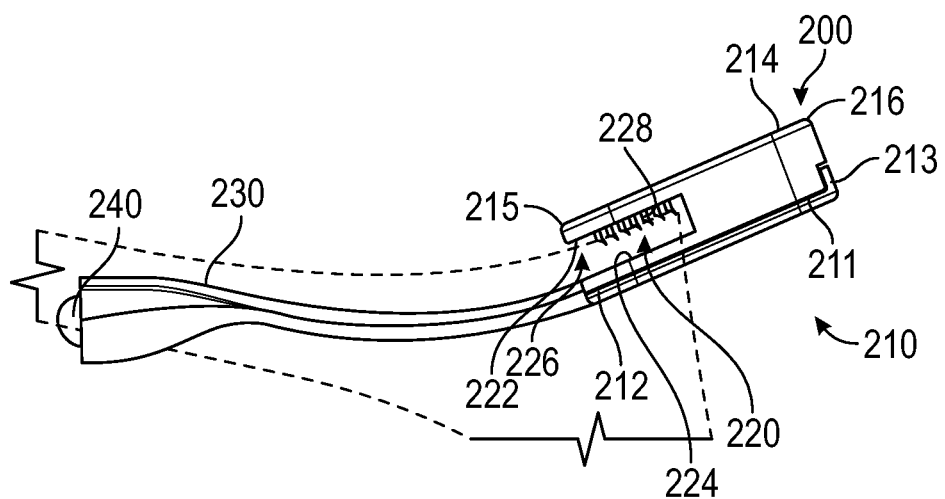
FIG. 3 is a side view of the lighting module of FIG. 2.

FIGS. 2 and 3 show a universal lighting module 200 according to certain exemplary embodiments. The lighting module 200 is configured to fit with a variety of medical speculum of various shapes, sizes, and configurations. The lighting module 200 may be used with disposable or reusable speculum. The lighting module 200 itself may be disposable or reusable.

As shown in FIG. 2, the lighting module 200 includes a housing portion 210, a clip portion 220, and an arm portion 230. The housing portion 210 is configured to house a power source for the lighting module. The housing portion 210 is enclosed by a base plate 211 (shown in FIG. 3), a top plate 214, and side walls 218. Base plate 211 includes a first end 212 which extends to the clip portion 220, and a second end 213. Top plate 214 includes a first end 215 which extends to the clip portion 220, and a second end 216. In some aspects, the top plate 214 includes a top surface 217 which is formed of a soft material, such as silicone or other similar material, and configured to provide a landing spot for fingers of an operator to provide an indication of proper hand placement and comfort for use without harming or irritating the fingers of the operator.

A clip portion 220 is formed adjacent to the housing portion 210 and is configured to attach the lighting module 200 to a speculum. The clip portion 220 is configured to provide a sufficiently sized surface area in contact with the speculum surface(s) for optimal grip to the speculum. The clip portion 220 comprises a top flange 222 which includes the first end 215 of the top plate 214 and a bottom flange 224 which includes the first end 212 of the base plate 211. A receiving area 226 is formed between the top flange 222 and bottom flange 224, which is configured to receive a portion of the speculum. One or both of the top flange 222 and the bottom flange 224 are at least partially deflectable, such that the distance between the top flange 222 and the bottom flange 224 is adjustable to accommodate a portion of the speculum that is wider than the natural dimensions of the receiving area 226. In this way, the clip is configured to be adjustable in order to fit most specula. The top flange 222 and the bottom flange 224 are naturally biased to maintain their original relationship therebetween. Accordingly, when the flanges are moved apart from one another and clipped over a portion of the speculum, a force is applied by the flanges to the speculum, which assists with maintaining the lighting module 200 on the speculum. In some aspects, a surface of the clip which faces the receiving area 226 also includes a grip 228, which is configured to provide pressure and/or increased resistance to movement of the lighting module 200 relative to a speculum when the lighting module 200 is attached on the speculum. The grip 228 may be a texturized material, such as a material having ridges, grooves, bumps, or flanges extending therefrom, as shown in the embodiment of FIG. 3. In other aspects, the grip 228 may be an extended portion of the flange such that the receiving area 226 has a decreased diameter in the area of the grip, such as in the embodiment of FIG. 2. In yet another aspect, the grip may be any material having increased frictional properties relative to the material of the module 200 or speculum 100. The grip 228 is configured to prevent the lighting module 200 from slipping off of the speculum during use.

In some aspects, the lighting module 200 also includes an arm portion 230 extending from the clip portion 220, and particularly, from the bottom flange 224. The arm portion 230 is oriented at an angle Θ relative to the bottom flange 224. Angle Θ may be configured to be an adjustable angle or it may be configured to be a static angle. Angle Θ may be any suitable angle such that arm portion 230 is disposed against or near a top bill of a speculum when the lighting module 200 is inserted on the speculum 100. The arm portion 230 may be flexible. According to one aspect, the arm portion 230 is configured to be disposed against a surface of the top bill of the speculum. The arm portion 230 may be further configured to act as a spring to hold the clip 220 and keep the lighting module close to a top bill of a speculum.

FIGS. 4 and 5 show a universal lighting module 400 according to certain exemplary embodiments. The lighting module 400 is configured to fit with a variety of medical speculum of various shapes, sizes, and configurations. The lighting module 400 may be used with disposable or reusable speculum. The lighting module 400 itself may be disposable or reusable.

As shown in FIG. 4, the lighting module 400 includes a housing portion 410, a clip portion 420, and an arm portion 430. The housing portion 410 is configured to house a power source for the lighting module. The housing portion 410 is enclosed by a base housing 411 and housing cap 413 which associates with the base housing 411, such as in a snap-fit relationship. Base housing 411 includes clip portion 420, and particularly clip 422, and also extends to the arm portion 430. Housing cap 413 also extends between the housing portion 410 and the arm portion 430.

Figure 6:
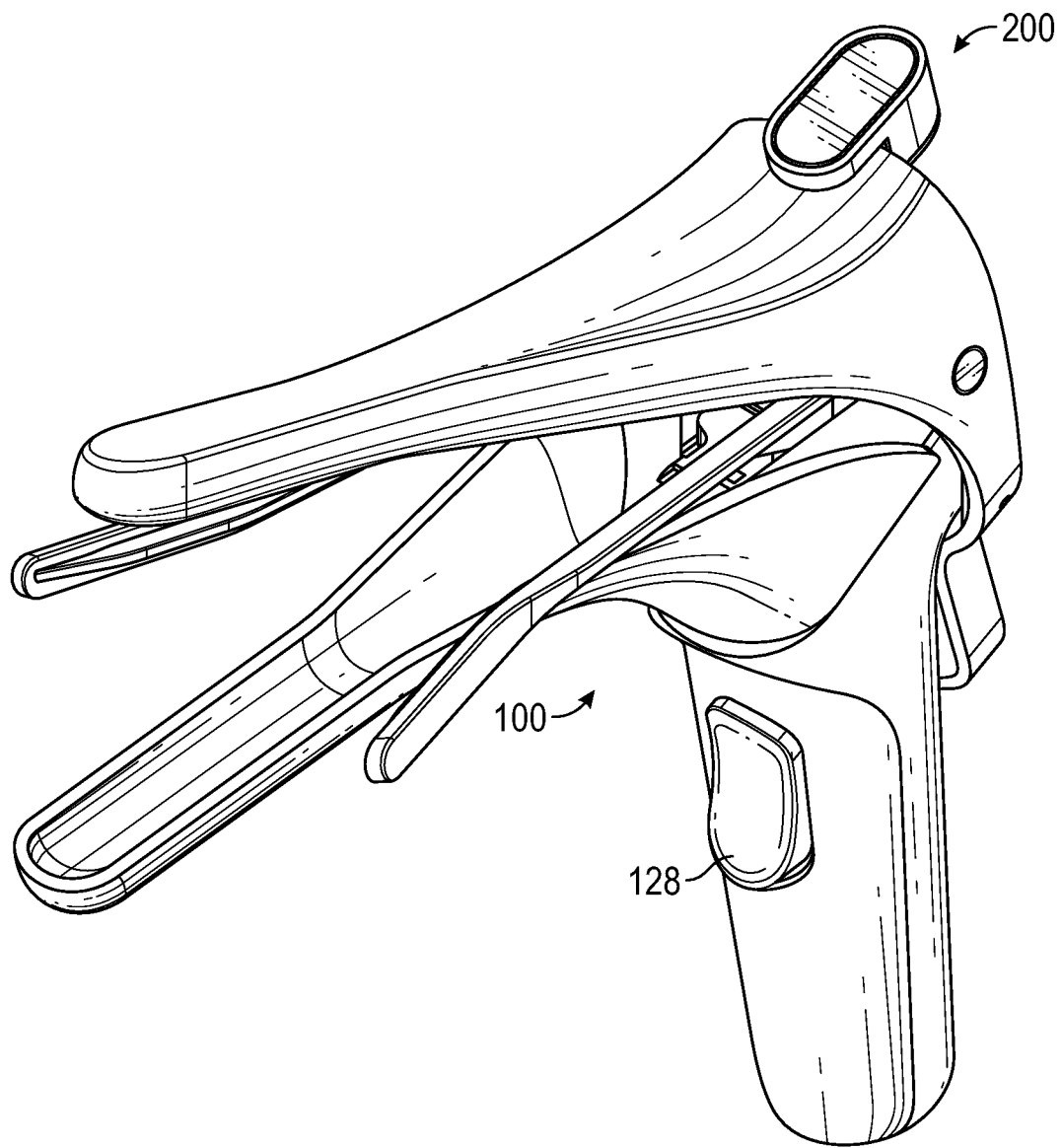
FIG. 6 is a front perspective view of a speculum assembly including the lighting module of FIG. 3.

Clip portion 420 is configured to attach the lighting module 400 to a speculum, as depicted in FIG. 6. The clip portion 420 is configured to provide a sufficiently sized surface area in contact with the speculum surface(s) for optimal grip to the speculum. The clip portion 420 comprises clip 422. A receiving area 426 is formed between the clip 422 and an opposing surface 424 of the base housing 411, which is configured to receive a portion of the speculum. The clip 422 is at least partially deflectable, such that the distance between the clip 422 and the surface 424 is adjustable to accommodate a portion of the speculum that is wider than the natural dimensions of the receiving area 426. In this way, the clip is configured to be adjustable in order to fit most specula or varying portions of a specula. Clip 422 is naturally disposed at an angle relative to and angling towards the surface 424. The clip 422 is naturally biased to maintain its original relationship to the surface 424. Accordingly, when the lighting module 400 is positioned over a medical device and clip 422 is moved apart from the surface 424, a force is applied by the clip to the speculum, which assists with maintaining the lighting module 400 on the speculum. In some aspects, a surface of the clip which faces the receiving area 426 also includes a grip, which is configured to provide pressure and/or increased resistance to movement of the lighting module 400 relative to a speculum when the lighting module 400 is attached on the speculum. The grip may be a texturized material, such as a material having ridges, grooves, bumps, or flanges extending therefrom. In another aspect, the grip may be any material having increased frictional properties relative to the material of the module 400 or speculum 100. The grip is configured to prevent the lighting module 400 from slipping off of the speculum during use.

In some aspects, the lighting module 400 also includes an arm portion 430 extending from the clip portion 420. The arm portion 430 is oriented at an angle Θ relative to the clip portion 420. Angle Θ may be configured to be an adjustable angle or it may be configured to be a static angle. Angle Θ may be any suitable angle such that arm portion 430 is disposed against or near a top bill of a speculum when the lighting module 400 is inserted on the speculum 100. The arm portion 430 may be flexible. According to one aspect, the arm portion 230 is configured to be disposed against a surface of the top bill of the speculum. The arm portion 430 may be further configured to act as a spring to hold the clip 420 and keep the lighting module close to a top bill of a speculum.

The lighting modules 200 and 400 also include a lighting element 240 at the distal end of the arm portion 230, 430, which is configured to be in electrical contact with the power source during operation. In some aspects, the lighting element 240 is a LED. The LED may be any color suitable for providing lighting to the cavity. In preferred embodiments, the LED is clear or white. Various sizes of LEDs can be used in lighting modules 200 and 400, such as 1 mm, 3 mm, 5 mm, and 10 mm LEDs. In order to limit current into the LED, so as not to burn out the LED, a resistor (not shown) is used in series with the LED in the lighting modules 200 and 400. The value of the resistor needed depends on the forward current and the forward voltage specifications of the LED (variable), and on the power source voltage. The LED may be flat or dome-shaped.

The lighting modules 200 and 400 also include an activation mechanism, shown by way of example as pull tab 250, configured to facilitate the powering of, or to provide power to, the lighting mechanism from the power source. Pull tab 250 may pass through the side wall 218 of the housing portion 210 by way of an aperture or slot formed therein, or through a gap created between base housing 411 and housing cap 413. In some aspects, the power source is at least one battery. Preferably, in some aspects, the power source is two batteries configured to be electrical contact with each other. Each battery (not shown) preferably has a voltage of about 3.0V, but batteries having other voltages may also be used. The lighting module also includes an activation mechanism which can be manipulated to cause the LEDs to go from an "off" state to an "on" state. In the embodiment shown, the activation mechanism is in the form of pull tab 250. According to this aspect, a portion of the pull tab 250 is positioned between the batteries, thereby preventing discharge of the batteries and keeping the LEDs "off." The pull tab 250 is configured to be pulled by the user to dislodge the pull tab 250 from between the batteries, thereby allowing the flow of current and providing power to the LEDs. In this embodiment, there is no mechanism for powering the LEDs off after they have been turned on. In some embodiments, the same activation mechanism may be used to power off the LEDs or there may be a second mechanism for powering off the LEDs.

Figure 7:
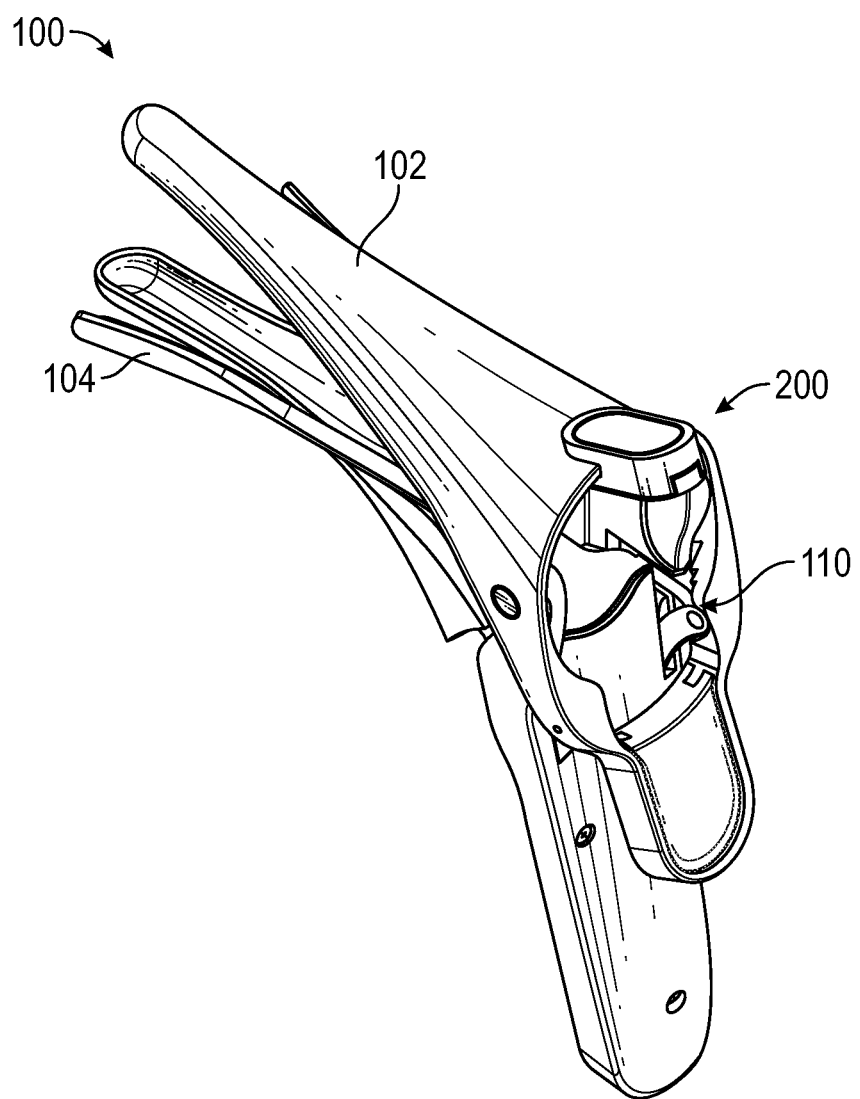
FIG. 7 is a rear perspective view of a speculum assembly as shown in FIG. 2.
Figure 8:
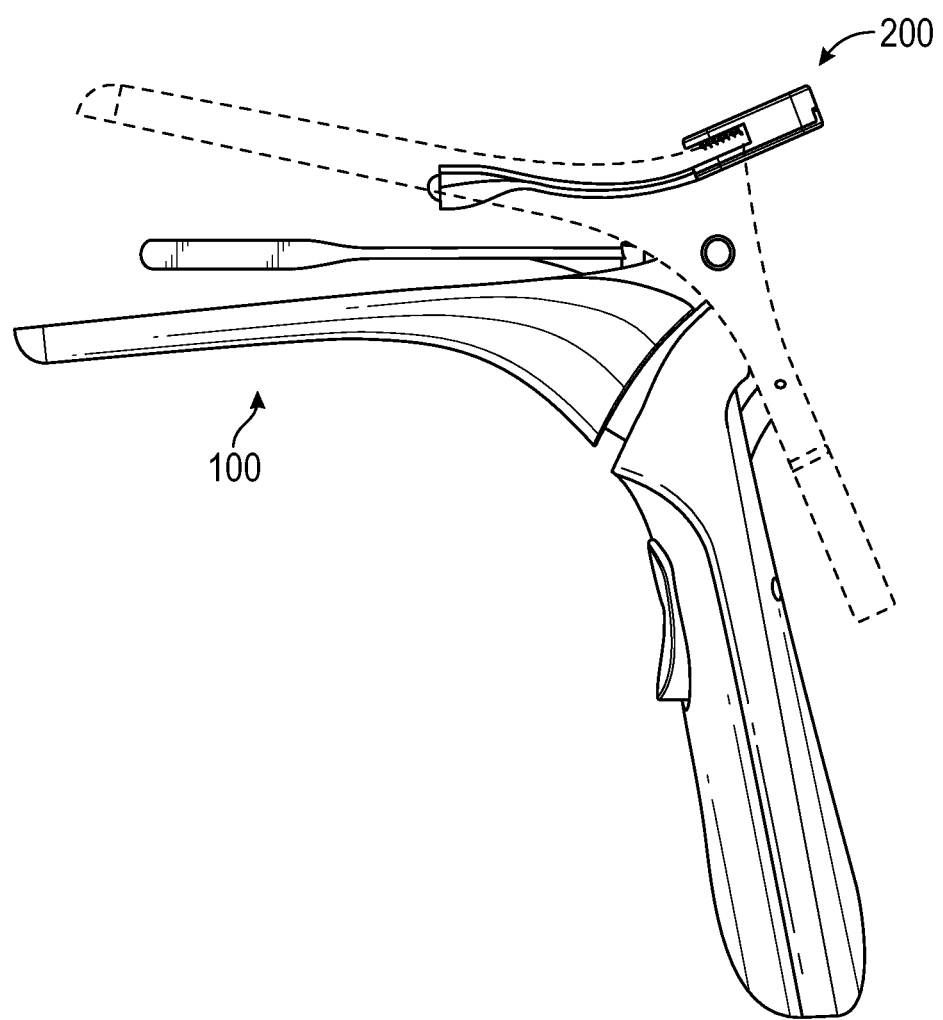
FIG. 8 is a side view of the speculum assembly as shown in FIG. 2.

FIG. 6 shows a speculum 100 with a lighting module 200 connected thereto, as disclosed herein. Similarly, lighting module 400 is configured to also connect with a speculum 100 in the same fashion as lighting module 200 shown in the figures. FIG. 7 shows an alternative view of a speculum 100 with a lighting module 200 connected thereto, according to the same embodiment. In one possible arrangement, as shown, the lighting module fits underneath a surface of a top bill 102 of the speculum 100. The lighting module is configured to be clipped to a top portion of the window frame such that the arm portion 230 is inserted through window 110 between the top bill 102 and a bottom bill 104 of the speculum 100. As shown in FIG. 8, the lighting module may be configured to align along an inner surface of the top bill of the speculum to hold the lighting module in place after being attached to the speculum 100 and/or in order to not obstruct the view of the user through the window 110. The lighting module 200 may be constructed in other configurations to fit along other portions of the speculum, or may be adjustable for other portions of the speculum.

Figure 9:
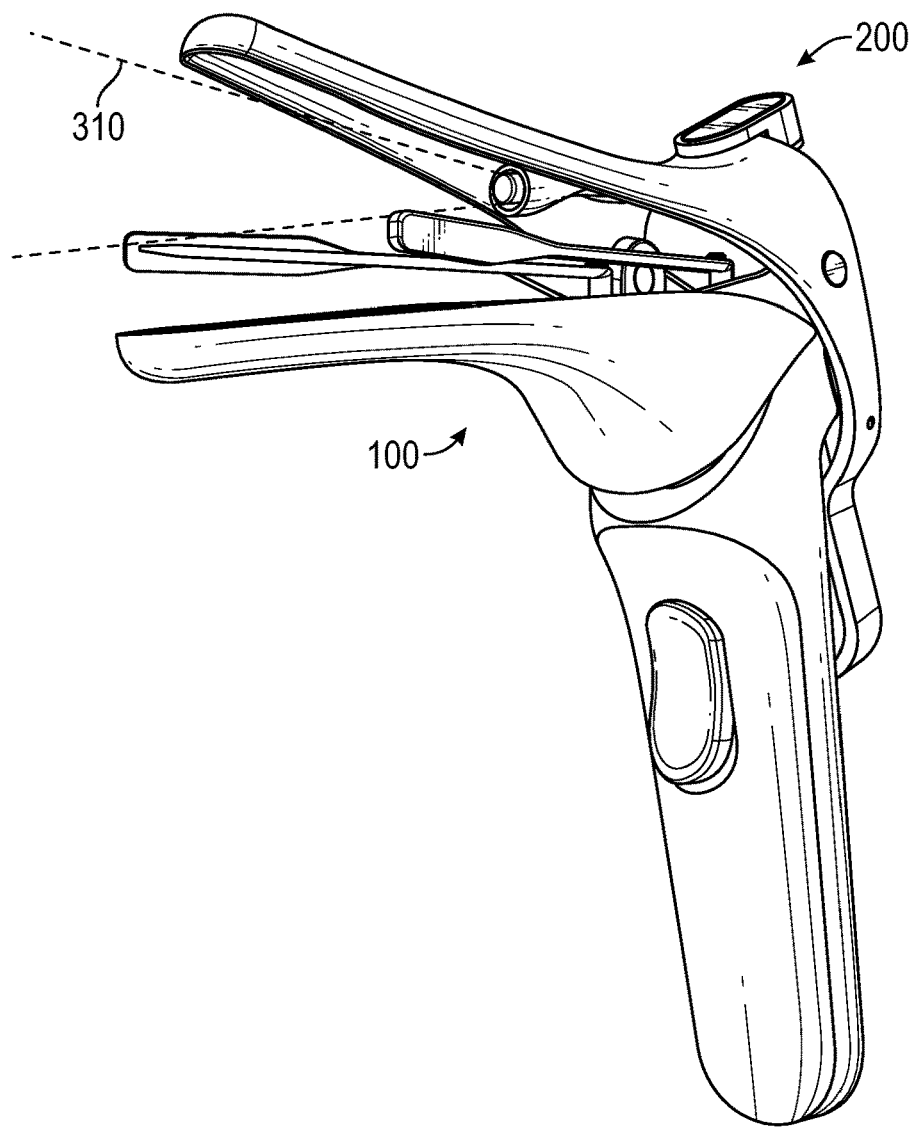
Figure 10:
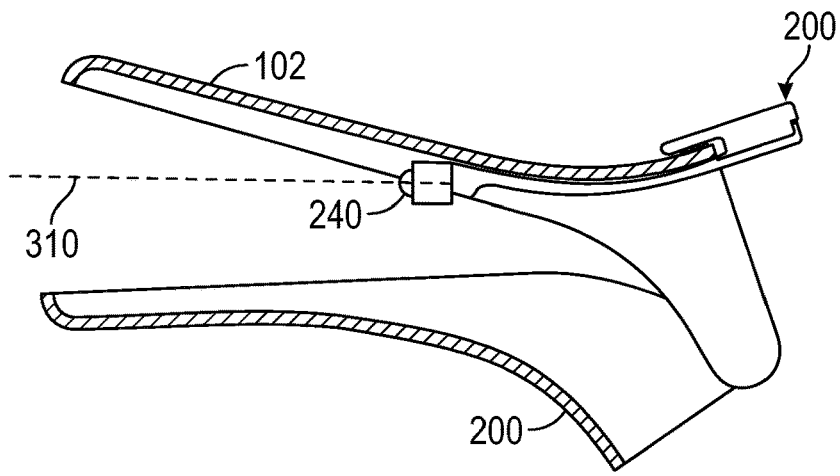
FIG. 10 is a cross-sectional side view of a top portion of a speculum assembly and the lighting module of FIG. 2 attached.

In FIGS. 9 and 10, the speculum 100 is shown in an open position, such as an open position when the speculum is in use in a body cavity of a patient. When the speculum is in an open position, an operator uses lighting element 240 to provide illumination in the body cavity. An operator can adjust a direction 310 of the illumination provided by light by adjusting the position of lighting module 200 on the speculum 100, or by adjusting the arm portion 230.

According to a still further embodiment of the present disclosure, a method for using the lighting module is disclosed. The method includes inserting a speculum into a body cavity of a patient, attaching a lighting module 200 or 400 to the speculum 100, and turning on the lighting element 240 of the lighting module 200 or 400. The method may further include adjusting a position to which a lighting element 240 of the lighting module 200 or 400 points. The steps described above may be completed in any order and are not limited to the order in which they were presented.

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the technology should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the terms "comprising" and "having" should, respectively, be interpreted as "comprising at least" and "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an." In general, "a" and/or "an" should be interpreted to mean "at least one" or "one or more"; the same holds true for the use of definite articles used to introduce claim recitations.

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The technology disclosed herein has numerous applications and while particular embodiments of the technology have been described in detail, it will be apparent to those skilled in the art that the disclosed embodiments may be modified given the design considerations discussed herein. Therefore, the foregoing description is to be considered exemplary rather than limiting, and the true scope of the invention is that defined in the following claims.

What is claimed is:

1. A lighting module for a speculum comprising:
   a housing portion;
   a clip portion comprising a receiving space for receiving an upper portion of a window frame of the speculum, the opening of the window frame forming a viewing window when a top bill and a bottom bill of the speculum are in an open position, the upper portion of the window frame of the speculum proximate to the top bill of the speculum, the clip portion configured to be clipped to the upper portion of the window frame of the speculum when the upper portion of the window frame of the speculum is received by the clip portion;
   an arm portion extending from the clip portion and comprising a light emitting diode (LED) at a distal end of the arm portion, the arm portion inserted through the viewing window formed by the window frame, a length of the arm portion forming an obtuse angle with a length of the clip portion so that the arm portion is configured to extend from the clip portion and be disposed against or near an inner surface of the top bill of the speculum;
   a power source contained in the housing portion electrically connected to the LED; and
   an activation mechanism for activating the LED by providing power to the LED.

2. The lighting module of claim 1,
   wherein the activation mechanism is a pull tab provided between a first and a second battery to prevent discharge of the batteries prior to operation of the LED; and
   wherein when the pull tab is removed, the first battery and the second battery become electrically coupled to provide power to the LED.

3. The lighting module of claim 1, wherein the arm portion is configured to be disposed against the inner surface of the top bill of the speculum.

4. The lighting module of claim 1, wherein the arm portion is adjustable.

5. The lighting module of claim 1, wherein the arm portion is flexible.

6. The lighting module of claim 1, wherein the clip portion comprises a clip, and wherein the clip is deflectable such that the receiving space is adjustable.

7. The lighting module of claim 1, wherein the clip portion comprises a first flange extended from the housing portion and a second flange extending from the housing portion, and wherein at least one of the first flange and the second flange is deflectable such that the receiving space is adjustable.

8. The lighting module of claim 1, wherein a top surface of the lighting module comprises a soft portion.

9. The lighting module of claim 1, wherein the clip portion comprises a grip on a surface facing the receiving space.

10. The lighting module of claim 9, wherein the grip is a texturized material.

11. The lighting module of claim 9, wherein the grip is an extended portion of a first flange or a second flange that extends into the receiving space.

12. The lighting module of claim 1, wherein the power source is at least one battery.

13. The lighting module of claim 12, wherein the power source is two batteries electrically connected together.

14. The lighting module of claim 1, wherein the lighting module is disposable.

15. The lighting module of claim 1, wherein the lighting module is reusable.

16. A speculum assembly, comprising:
    a speculum; and
    a lighting module, comprising:
      a housing portion;
      a clip portion comprising a receiving space for receiving an upper portion of a window frame of the speculum, the opening of the window frame forming a viewing window when a top bill and a bottom bill of the speculum are in an open position, the upper portion of the window frame of the speculum proximate to the top bill of the speculum, the clip portion configured to be clipped to the upper portion of the window frame of the speculum when the upper portion of the window frame of the speculum is received by the clip portion;
      an arm portion extending from the clip portion and comprising a light emitting diode (LED) at a distal end of the arm portion, the arm portion inserted through the viewing window formed by the window frame, a length of the arm portion forming an obtuse angle with a length of the clip portion so that the arm portion is configured to extend from the clip portion and be disposed against or near an inner surface of the top bill of the speculum;
      a power source contained in the housing portion and electrically connected to the LED; and
      an activation mechanism for activating the LED by providing power to the LED.

17. The lighting module of claim 1, wherein a width of the clip portion is narrower than a width of the viewing window, enabling repositioning of the clipped portion along the upper portion of the window frame.

18. The speculum assembly of claim 16, wherein the obtuse angle of the arm portion relative to the clip portion is adjustable, and wherein adjusting the obtuse angle of the arm portion relative to the clip portion adjusts a direction of the illumination from the LED.

19. The lighting module of claim 1, wherein the clip portion is proximal to the window frame of the speculum, and the arm portion is distal to the window frame when the clip portion is clipped to the upper portion of the window frame of the speculum.

20. The lighting module of claim 1, further comprising a power source contained in a housing portion, the housing portion adjoining the clip portion, the housing portion between the upper bill of the speculum and the lower bill of the speculum when the clip portion is clipped to the upper portion of the window frame of the speculum.

21. The lighting module of claim 1, wherein the LED is positioned at the distal end of the arm portion, the arm portion located between the upper bill of the speculum and the lower bill of the speculum when the clip portion is clipped to the upper portion of the window frame of the speculum.

\* \* \* \* \*